(12) United States Patent
Dequin et al.

(10) Patent No.: US 9,017,989 B2
(45) Date of Patent: Apr. 28, 2015

(54) MEANS FOR REDUCING ACETOIN BUILDUP IN ALCOHOLIC FERMENTATION MEDIA

(76) Inventors: Sylvie Dequin, Montpellier (FR); Maryam Ehsani, Montpellier (FR); Maria Rosario Fernández Gallegos, Barberà del Vallès (ES); Josep A. Biosca, Barcelona (ES); Anne Ortiz-Julien, Gagnac-sur-Garonne (FR)

( * ) Notice: Subject to any disclaimer, the term of this patent is extended or adjusted under 35 U.S.C. 154(b) by 404 days.

(21) Appl. No.: 12/451,339

(22) PCT Filed: May 6, 2008

(86) PCT No.: PCT/IB2008/051761
§ 371 (c)(1),
(2), (4) Date: Nov. 6, 2009

(87) PCT Pub. No.: WO2008/135950
PCT Pub. Date: Nov. 13, 2008

(65) Prior Publication Data
US 2010/0086644 A1    Apr. 8, 2010

(30) Foreign Application Priority Data
May 7, 2007  (FR) ..................... 07 03279

(51) Int. Cl.
| | | |
|---|---|---|
| C12N 1/00 | (2006.01) |
| C12N 1/19 | (2006.01) |
| C12G 3/02 | (2006.01) |
| C12G 1/022 | (2006.01) |
| C12G 3/08 | (2006.01) |
| C12N 9/04 | (2006.01) |
| C12P 7/18 | (2006.01) |

(52) U.S. Cl.
CPC ................ C12G 3/02 (2013.01); C12G 1/0203 (2013.01); C12G 3/08 (2013.01); C12G 2200/11 (2013.01); C12N 9/0006 (2013.01); C12P 7/18 (2013.01)

(58) Field of Classification Search
None
See application file for complete search history.

(56) References Cited

FOREIGN PATENT DOCUMENTS

WO          96/41888         12/1996

OTHER PUBLICATIONS da Silva et al. Influence of plasmid origin and promoter strength in fermentations of recombinant yeast. Biotechnol Bioeng. Feb. 20, 1991;37(4):318-24.*
International Search Report for PCT/IB2008/051761, mailed Oct. 6, 2008.
Gonzalez et al., "Characterization of a (2R, 3R)-2, 3-butanediol Dehydrogenase as the *Saccharomyces cerevisiae* Yal060W Gene Product. Disruption and Induction of the Gene", Journal of Biological Chemistry, American Society of Biolochemical Biologists, Birmingham, US, vol. 275, No. 46, Nov. 2000, pp. 35876-35885.
Remize et al., "Glycerol Overproduction by Engineered *Saccharomyces cerevisiae* Wine Yeast Strains Leads to Substantial Stimulation of Fermentation and to a Stationary Phase", Applied and Environmental Microbiology, vol. 65, No. 1, Jan. 1999, pp. 143-149.

* cited by examiner

*Primary Examiner* — Michele K Joike
(74) *Attorney, Agent, or Firm* — Nixon & Vanderhye P.C.

(57) ABSTRACT

The invention relates to yeasts expressing the gene BDH1 coding for Bdh1p, characterized in that they catalyze, in an alcoholic fermentation medium, the reduction of acetoin into 2,3-butanediol by a rate at least twice higher than that of the initial stem. The invention can particularly be used for the fermentation of fruit juice and for producing 2,3-butanediol.

9 Claims, 7 Drawing Sheets

Figure 1:
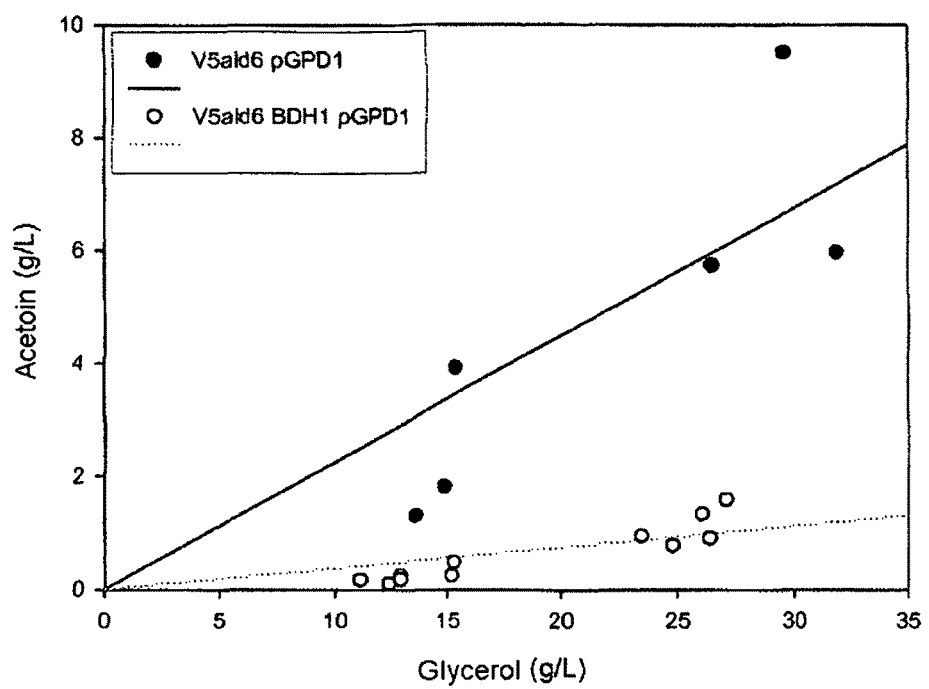

```
  1   MRALAYFKKGDIHFTNDIPRPEIQTDDEVIIDVSWCGICGSDLHEYLDGPIFMPKDGECH   60
  1   MRALAYFKKGDIHFTNDIPRPEIQTDDEVIIDVSWCGICGSDLHEYLDGPIFMPKDGECH   60

61   KLSNAALPLAMGHEMSGIVSKVGPKVTKVKVGDHVVVDAASSCADLHCWPHSKFYNSKPC  120
 61   KLSNAALPLAMGHEMSGIVSKVGPKVTKVKVGDHVVVDAASSCADLHCWPHSKFYNSKPC  120

121   DACQRGSENLCTHAGFVGLGVISGGFAEQVVVSQHHIIPVPKEIPLDVAALIEPLSVTWH  180
121   DACQRGSENLCTHAGFVGLGVISGGFAEQVVVSQHHIIPVPKEIPLDVAALIEPLSVTWH  180

181   AVKISGFKKGSSALVLGAGPIGLCTILVLKGMGASKIVVSEVAERRIEMAKKLGVEVFNP  240
181   AVKISGFKKGSSALVLGAGPIGLCTILVLKGMGASKIVVSSRSERRIEMAKKLGVEVFNP  240

241   SKHGHKSIEILRGLTKSHDGFDYSYDCSGIQVTFETSLKALTFRGTATNIAVWGPKPVPF  300
241   SKHGHKSIEILRGLTKSHDGFDYSYDCSGIQVTFETSLKALTFRGTATNIAVWGPKPVPF  300

301   QPMDVTLQEKVMTGSIGYVVEDFEEVVRAIHNGDITMEDCKQLITGKQRIEDGWEKGFQE  360
301   QPMDVTLQEKVMTGSIGYVVEDFEEVVRAIHNGDITMEDCKQLITGKQRIEDGWEKGFQE  360

361   LMDHKESNVKILLTPNNHGEMK   382
361   LMDHKESNVKILLTPNNHGEMK   382
```

FIGURE 3

US 9,017,989 B2

MEANS FOR REDUCING ACETOIN BUILDUP IN ALCOHOLIC FERMENTATION MEDIA

This application is the U.S. national phase of International Application No. PCT/IB2008/051761, filed 6 May 2008, which designated the U.S. and claims priority to French application Ser. No. 07/03279, filed 7 May 2007, the entire contents of each of which are hereby incorporated by reference.

The invention relates to yeasts and to fermentation methods using these yeasts, for reducing acetoin buildup in alcoholic fermentation media.

Over the past fifteen years or so, scientific knowledge and know-how in viticulture and enology have led to a very significant improvement in the organoleptic qualities of wines. Current wine-making practices favor the production of wines with a high qualitative potential by delaying the time of the grape harvest. A major consequence of this is an increase in the sugar content of the musts, and therefore in the alcohol content of the wines (frequently greater than 14°). This drift, encountered in most producing regions, openly poses many problems for the wine-making industry throughout the world. Excessive alcohol contents are in fact not very compatible with the preoccupations of health and of well-being of consumers, and are, moreover, the subject of taxation in certain countries.

As a result, there is an increasing demand for methods and tools that make it possible to reduce the alcohol content of wines and other alcoholic beverages. Physical approaches (for example, vacuum distillation) are increasingly used, but are not very compatible with the maintaining of satisfactory organoleptic quality.

One biological solution would be based on the use of yeast strains with a low alcohol yield.

For example, *Saccharomyces cerevisiae* yeasts, in particular enological *Saccharomyces cerevisiae* yeasts, convert sugars to alcohol with a yield of 0.47 g/g, which varies little according to the strain used. As a result, the production of a *Saccharomyces cerevisiae* yeast with a low alcohol yield requires the implementation of genetic strategies aimed at diverting a part of the sugars to the formation of other by-products.

Several genetic engineering approaches have been implemented in order to divert a part of the sugars to the production of by-products other than ethanol. These approaches have been based on the modification of the activity of enzymes involved in the synthesis of glycerol or in the use of pyruvate. For example, the overproduction of glycerol, obtained by overexpression of GPD1 or GPD2 encoding glycerol-3-phosphate dehydrogenase (Michnick et al., 1997; Remize et al., 1999; international patent application WO 96/41888) has thus made it possible to reduce the ethanol content by 1 to 2°. It is, however, accompanied by major modifications of the level of production of other metabolites, including some which are undesirable in wine, especially acetate and acetoin (3-hydroxy-2-butanone). The production of acetate can be reduced by deleting ALD6 which encodes an acetaldehyde dehydrogenase. On the other hand, no strategy has for the moment been described for reducing acetoin buildup. This compound builds up at a rate of several grams per liter, although it is unfavorable, for example in wine, at more than 150 mg/l (olfactory detection threshold).

The solution proposed by the inventors consists in converting the acetoin that is produced into 2,3-butanediol, a compound considered to be neutral from an organoleptic point of view, the detection threshold thereof in wine being greater than 12 g/l.

The production of 2,3-butanediol from acetoin is carried out by the butanediol dehydrogenase (Bdh1p) enzyme encoded by BDH1.

The 2,3-butanediol production pathway contributes to the intracellular NAD$^+$/NADH redox balance. In bacteria, this pathway can also be involved in the regulation of intracellular pH.

2,3-Butanediol is produced in several forms: (2R,3R)-2,3-butanediol and (2S,3S)-2,3-butanediol, two optically active forms, (2R,3S)-2,3-butanediol and (2S,3R)-2,3-butanediol, corresponding to the meso forms.

The butanediol dehydrogenase encoded by BDH1 is the main enzyme involved in the production of 2,3-butanediol. It is responsible for the formation of all the (2R,3R)-2,3-butanediol and a part of the (meso)-2,3-butanediol, from R-acetoin and S-acetoin, respectively. Since Bdh1p has, moreover, a greater affinity for acetoin ($Km_{acetoin}$: 4.5 mM, $Km_{2,3-butanediol}$: 14 mM), the reaction is strongly shifted in the direction of the formation of 2,3-butanediol.

In the approach followed, the inventors have considered that the level of synthesis of 2,3-butanediol dehydrogenase is a factor that limits the reaction for conversion of acetoin to 2,3-butanediol. They have also retained the fact that a reduced availability of NADH could prevent a more effective conversion of acetoin. A strategy of overexpression of BDH1 and of site-directed mutagenesis of BDH1 has therefore been implemented in order to change its cofactor specificity from NADH to NADPH.

Their studies have thus made it possible to transform *Saccharomyces* strains and to render them capable of efficiently converting acetoin to 2,3-butanediol over the course of an alcoholic fermentation, even when the acetoin is produced in large amounts (several g/l).

The objective of the invention is therefore to provide novel yeast strains genetically transformed so as to overexpress BDH1 and exhibiting a modified, cofactor specificity, in order to produce larger amounts of 2,3-butanediol from acetoin.

The invention is also directed toward providing a method for obtaining such strains.

The objective of the invention is also to take advantage of the properties of these transformed yeast strains in a method of alcoholic fermentation and also for the production of 2,3-butanediol.

The yeast strains of the invention are yeasts which overexpress, relative to the initial strain, the BDH1 gene encoding Bdh1p.

These strains are characterized in that they catalyze, in an alcoholic fermentation medium, the reduction of acetoin to 2,3-butanediol according to a rate that is at least twice that of the initial strain.

They are more especially strains that have been genetically transformed and/or mutated in such a way as to obtain an acetoin-to-2,3-butanediol conversion rate that is at least twice that of the initial strain.

The term "initial strain" is intended to mean a strain before overexpression or modification of the BDH1 gene.

The invention is thus directed toward yeast strains as defined above, genetically transformed so as to overexpress BDH1, by means of regulatory sequences suitable for increasing the expression of said gene. Such transformed strains contain at least 2 copies of the BDH1 gene. Any promoter that is active in the host in which it is desired to obtain the expression of this gene may be used, preferably promoters described as strong (encoding strongly expressed genes) under alcoholic fermentation conditions. This is the case, for example, of glycolytic genes strongly expressed in fermentation, such as ADH1 (alcohol dehydrogenase), PGK1

(phosphoglycerate kinase) or TDH3 (glyceraldehyde dehydrogenase), or the TEF1 transcription factor gene, but many others also exist.

The invention is also directed toward strains in which the BDH1 gene comprises one or more mutations in such a way as to encode a Bdh1p protein in which one or more amino acids are mutated.

Advantageously, such strains comprise one or more mutations in the BDH1 gene in order to exhibit an increased affinity for the NADPH cofactor instead of NADH.

The choice of amino acids to be modified is based on the fact that NAD(H) differs from NADP(H) in terms of the phosphate group esterified at the 2'-position of the ribose of adenosine. As a result, the amino acids that interact with this group are candidates for the cofactor specificity change. The residue which determines the NAD(H) specificity is aspartate (Asp) or glutamate (Glu), which form hydrogen bonds with the 2'- and 3'-hydroxyl groups in the ribosyl part of the coenzyme. NADP(H)-dependent dehydrogenases have a smaller and neutral residue, such as glycine (Gly), alanine (Ala) and serine (Ser), at the same position. In addition, an adjacent arginine residue (Arg) enables good interaction with the phosphate group of NADP(H).

Thus, advantageous replacements in accordance with the invention concern the Glu(E)221 residue replaced with Ser (S), the Ile(I)222 residue replaced with Arg(R) and the Ala (A)223 residue replaced with Ser, using as a basis the structure of the NADPH-dependent Adh6p enzyme of S. cerevisiae (the positions are denoted according to the amino acid sequence of Bdh1p of Saccharomyces cerevisiae S288C).

The modification(s) of Glu(Asp)221 and/or Ile(val)222 and/or Ala223 and any possible combination of these three modifications are also part of the field of the invention.

The first residue may also be a serine (as in the example), or any small, neutral amino acid such as Gly or Ala.

The invention is also directed toward strains as defined above, genetically modified so as to overexpress BDH1 in an alcoholic fermentation medium, by means of a strong yeast promoter, and comprising one or more mutations in BDH1 in order to exhibit a cofactor specificity for NADPH instead of NADH.

In one preferred embodiment of the invention, the yeast strains which produce acetoin are strains that overproduce glycerol. They are in particular strains containing the overexpressed GPD1 gene or the overexpressed GPD2 gene, for example obtained by transformation of the strains with the pVT100U-ZEO-URA3-GPD1 plasmid or by in situ exchange of its promoter with a strong promoter.

In another embodiment of the invention, the yeast strains are genetically modified in such a way as to reduce the production of acetate (in addition to the overexpression of GPD1). More particularly, they are strains in which the ALD6 gene and, where appropriate, copies thereof has (have) been deleted.

Preferred strains belong to the Saccharomyces genus and comprise, in particular, the species Saccharomyces cerevisiae, Saccharomyces bayanus, Saccharomyces uvarum and Saccharomyces kudriavzevii.

Other preferred strains belong to the non-Saccharomyces genus.

The invention is also directed toward the hybrids of the strains defined above.

The invention is also directed toward a method for obtaining the yeast strains mentioned above.

This method advantageously takes advantage of the genetic engineering and site-directed mutagenesis techniques. By way of example, mention will be made of the use of an oligonucleotide comprising the desired target mutations in order to modify the BDH1 gene of a yeast strain, and the transformation of the strain with an amplified fragment, the amplification of a region of the gene comprising the mutations, or alternatively crossing between strains, starting from a strain comprising, for example, the desired mutations in order to transfer them into another.

A subject of the invention is also a method of fermentation, characterized by the addition of a transformed yeast strain as defined above to the fermentation medium.

The fermentation medium is in particular a must, advantageously a grape juice.

According to one aspect of great importance, the 2,3-butanediol obtained using the yeast strains of the invention constitutes an important compound for a variety of chemically based materials and liquid fuels.

This compound may result, by dehydration, in the formation of methyl ethyl ketone, that can be used as a liquid fuel additive.

The 2,3-butanediol may also be converted to 1,3-butanediene, a compound that is used in the production of synthetic gum. Other derivatives, for uses, for example, as antifreezes (levo form), solvents and plastics, may also be prepared from 2,3-butanediol. In addition, it may be added to food products as a flavor after conversion to diacetyl by dehydrogenation.

The esterification of butanediol leads to the formation of polyurethane precursors for use in medicaments, cosmetic products and lotions, etc.

The use of the yeast strains for producing 2,3-butanediol, in particular in the applications mentioned above, is also part of the field of the invention.

In particular, the invention provides means for obtaining a higher 2,3-butanediol yield and productivity in general, but also for obtaining pure stereoisomers, in large amounts, instead of a mixture of isomers.

The yeast strains of the invention also make it possible to reduce the amount of diacetyl produced. They are advantageously used to this effect, in particular in fermented beverages.

Figure 2:
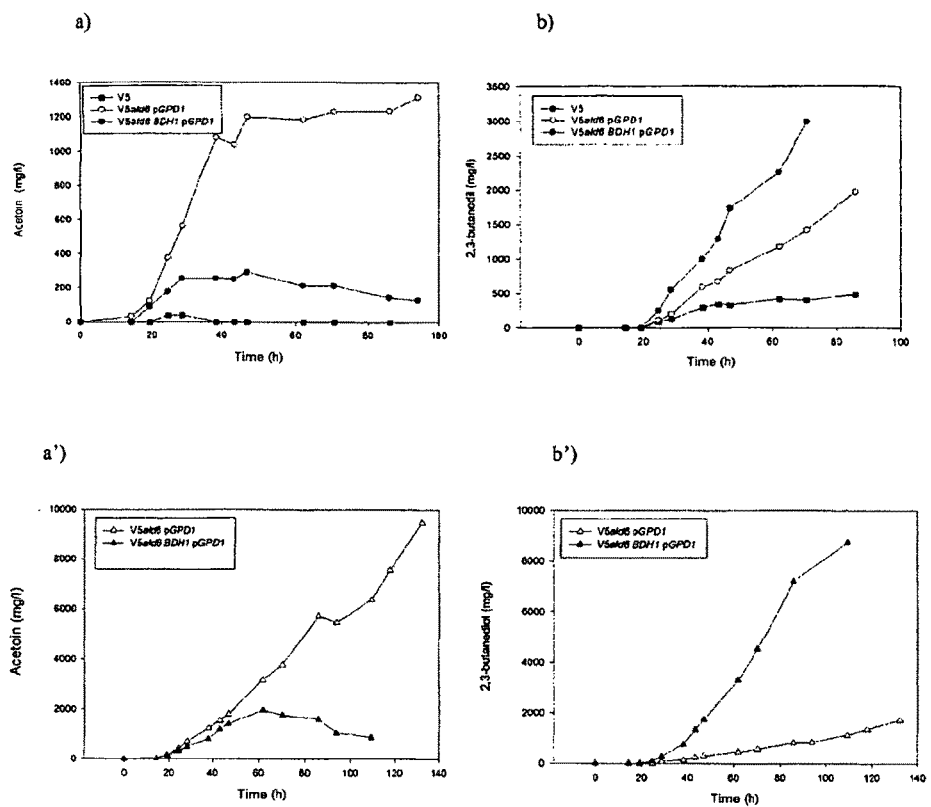
Figure 4:
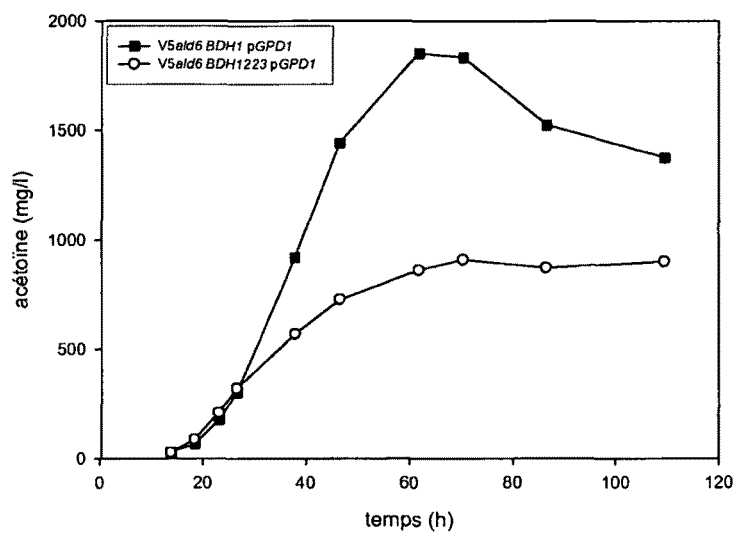
Figure 5:
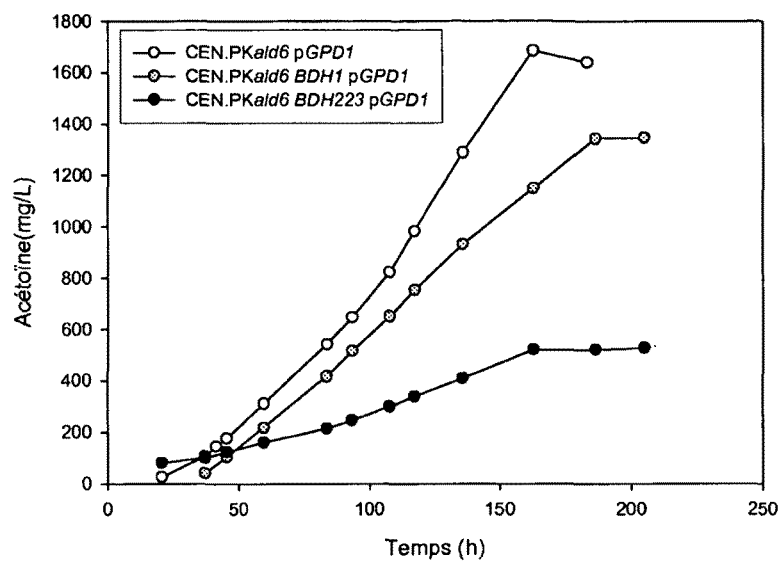
Figure 6:
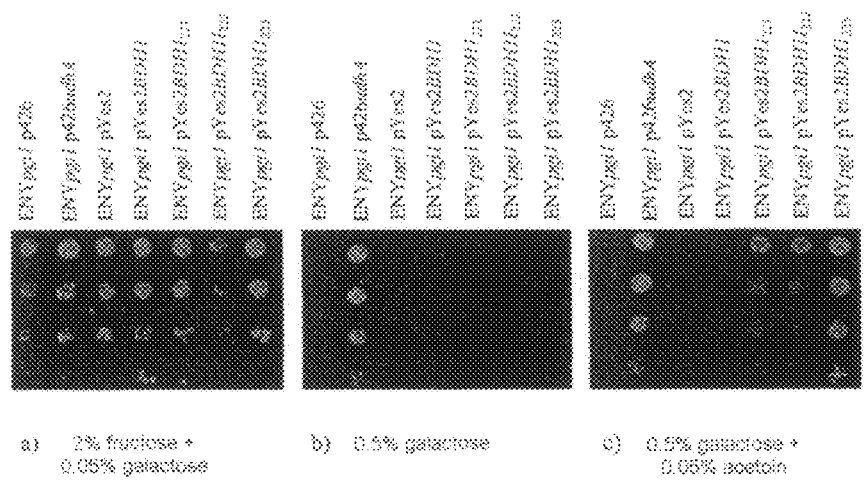

Other characteristics and advantages of the invention are given in the exemplary embodiments which follow. In these examples, reference is made to FIGS. 1 to 7 which represent, respectively:

FIG. 1: the effect of the overexpression of BDH1 on the production of acetoin by the V5ald6 BDH1 pGPD1 strain for varying glycerol concentrations;

FIG. 2: the production of acetoin (a and a') and of 2,3-butanediol (b and b') over the course of fermentation for the V5 and V5ald6 pGPD1 and V5ald6 BDH1 pGPD1 strains under conditions (i): a, b and (ii): a', b';

FIG. 3: sequence alignment of BDH1 (in bold) (SEQ ID NO:10) and BDH1$_{223}$ (SEQ ID NO:11). In gray: the change of 3 amino acid residues E221S/V222R/A223S inducing a reversion of the cofactor specificity in Bdh1p;

FIG. 4: acetoin formation in the V5ald6 BDH1 pGPD1 (black) and V5ald6 BDH1$_{223}$ pGPD1 (white) strains over the course of a fermentation;

FIG. 5: the final formation of acetoin in the CEN.PKald6 pGPD1 (white), CEN.PKald6 BDH1 pGPD1 (gray) and CEN.PKald6 BDH1$_{223}$ pGPD1 (black) strains at the end of several fermentations;

FIG. 6: the functioning of mutant forms in vivo; and

Figure 7:
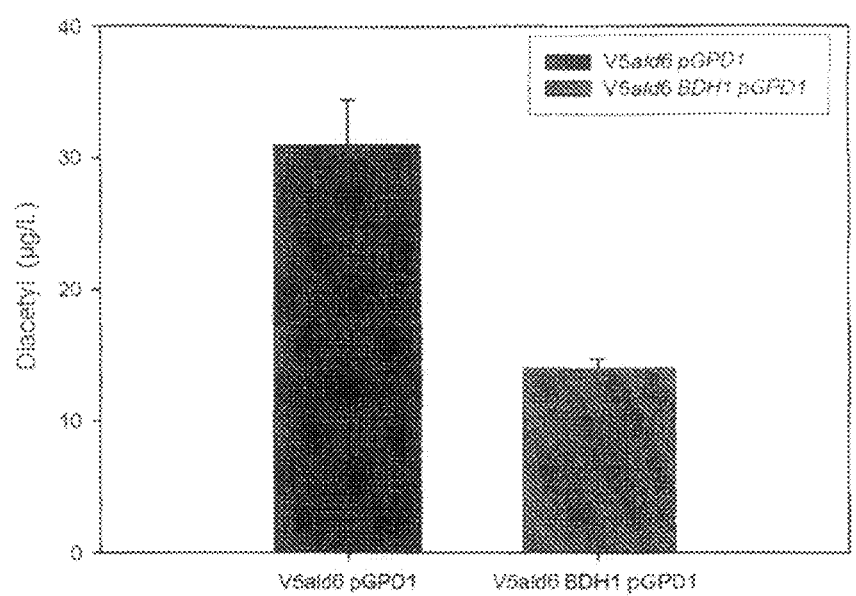

FIG. 7: the reduction of diacetyl formation by overexpression of BDH1.

Obtaining *Saccharomyces Cerevisiae* Strains Overexpressing BDH1

The BDH1 promoter was replaced with the TDH3 promoter in situ, using the short flanking homologous (SFH) PCR (polymerase chain reaction) technique (Guldener et al., 1996).

A fragment constituted of the kanMX module, which carries the kanR gene conferring resistance to the G418$^R$ antibiotic, and of the TDH3 promoter was amplified by PCR from the bacterial plasmid pUG6-NOXE (Heux et al., 2005) using the oligonucleotides having the sequences, respectively, SEQ ID No. 1 and SEQ ID No. 2, carrying a sequence homologous to pUG6-NOXE and a flanking sequence (in italics) homologous to the chromosomal target region (BDH1 promoter).

SEQ ID No. 1:
5' CTTTCCTCCT TACGGGGTCC TAGCCTGTTT CTCTTGATAT

GCAGGTCGAC AACCCTTAAT 3'

SEQ ID No. 2:
5' AGTGAATATC ACCCTTCTTG AAATATGCCA AAGCTCTCAT

TCGAAACTAA GTTCTTGGTGT 3'

Experimental conditions used for the PCR:

| | |
|---|---|
| Oligonucleotide SEQ ID No. 1 | 5 µl (20 pmol) |
| Oligonucleotide SEQ ID No. 2 | 5 µl (20 pmol) |
| DyNazyme EXT buffer 10X + 15 mM MgCl$_2$ (Finnzymes, Finland) | 5 µl |
| 2 mM dNTP | 5 µl |
| pUG6-NOXE | 1 µl (25 ng) |
| H$_2$O | 28.25 µl |
| DyNazyme EXT (Finnzymes, Finland) | 0.75 µl |

30 cycles (45 sec 94° C., 30 sec 55° C., 2 min 72° C.) on a Perkin-Elmer Cetus model 9600 amplifier.

The PCR product obtained was precipitated with ethanol in the presence of salts. 3 µg of the precipitated DNA were used to transform the *S. cerevisiae* yeast strains V5 and V5ald6. The V5 strain (MATa, ura3) is derived from an enological strain. The V5 strain and the V5ald6 strain (Remize et al., 1999) in which the two copies of the ALD6 gene were deleted were transformed by the lithium acetate method (Schiestl and Gietz, 1989). The transformants were selected on YPD G418$^R$ dishes. The integration of the TDH3 promoter in place of the BDH1 promoter was verified by PCR.

Results

The results obtained show that the V5 BDH1 strain has the same growth and fermentation rate as the V5 control strain. The measurement of the BDH activity during the exponential phase and the stationary phase shows that the BDH enzymatic activity of the strain overexpressing BDH1 is approximately 30 times greater than that of the wild-type strain (average specific activity V5:0.1 U/mg total protein; average specific activity V5 BDH1:3.2 U/mg total protein).

Effect of the Overexpression of BDH1 in Strains Overexpressing GPD1

The V5, V5ald6, V5 BDH1 and V5ald6 BDH1 strains were transformed with 10 ng of the multicopy vector pVT100U-ZEO-GPD1 (Remize et al., 1999) carrying the URA3 gene. The transformants were selected on YNB dishes supplemented with methionine (115 mg/l). After verification by PCR, four strains: V5 pGDP1, V5ald6 pGPD1, V5 BDH1 pGPD1 and V5ald6 BDH1 pGPD1, were obtained.

Effect of the Overproduction of BDH1p on Acetoin Synthesis

Culture conditions—The strains studied during fermentation under enological conditions are indicated in table 1 below.

TABLE 1

| Strain | Characteristics |
|---|---|
| V5 | *S. cerevisiae* strain derived from a MATA, ura3 enological yeast |
| V5 BDH1 | V5 strain overexpressing BDH1 |
| V5 pGPD1 | V5 strain overexpressing GPD1 |
| V5 BDH1 pGPD1 | V5 strain overexpressing BDH1 and GPD1 |
| V5ald6 pGPD1 | V5 strain ALD6-deleted and overexpressing GPD1 |
| V5ald6 BDH1 pGPD1 | V5 strain ALD6-deleted and overexpressing GPD1 and BDH1. |

The fermentations were carried out in 1.2-liter reactors (SGI, France) with a reaction volume of 1 liter. The MS medium was used for preculturing and culturing. It is a synthetic medium which simulates a standard grape must (Bely et al., 1990). The MS medium contains 20% glucose, 6 g/l of malic acid, 6 g/l of citric acid, and 460 mg/l of nitrogen, in the form of NH$_4$Cl (120 mg/l) and of amino acids (340 mg/l). The medium is supplemented with methionine (115 mg/l) and, if necessary, uracil (50 mg/l). The pH of the MS medium is 3.3. Anaerobiosis factors, ergosterol (7.5 mg/l), oleic acid (2.5 mg/l) and Tween 80 (0.21 g/l) are added. The precultures were prepared in 100 ml Erlenmeyer flasks containing 20 ml of medium at 28° C. with shaking (150 rpm) for 30 h. The reactors were inoculated using these precultures, at a cell density of 1×10$^6$ cells/ml, and maintained at a constant temperature of 28° C. with continuous shaking (300 rpm).

The culture samples were collected using a syringe. The fermentation data are expressed as a function of time.

Analytical methods—The growth was monitored by measuring the optical density at 600 nm and by counting the number of cells on a Coulter Counter instrument (ZBI) using an aliquot fraction of the culture medium.

The metabolites were assayed in the supernatant, after centrifugation, of the samples taken, at 13 000 rpm for 5 minutes. The glucose, glycerol, ethanol, pyruvate, succinate, acetate, α-ketoglutarate and 2-hydroxy-glutarate concentrations were determined by high pressure liquid chromatography (HPLC) using an HPX-87H column (Bio-Rad). The acetaldehyde concentration was determined by the enzymatic method described by Lundquist (1974). The acetoin and 2,3-butanediol concentrations were determined by gas chromatography as described by Michnick et al., 1997.

FIG. 1 shows the impact of the overexpression of BDH1 on acetoin production. In this example, the production of this compound was analyzed over the course of fermentation with V5ald6 pGPD1 and V5ald6 BDH1 pGPD1. Two different conditions of glycerol overproduction were used. Under conditions (i), no selection pressure was used to maintain the pVT100U-ZEO-GPD1 plasmid, resulting in a moderate overproduction of glycerol, reaching 10-15 g/l. Under conditions (ii), the V5 BDH1 pGPD1 and V5ald6 BDH1 pGPD1 strains were cultured in the absence of uracil, enabling the plasmid to be maintained throughout the fermentation, generating a very high overproduction of glycerol, 20-30 g/l.

Under the two conditions tested, (i) and (ii), the overexpression of BDH1 allows a drastic decrease in acetoin production of up to 90% relative to the level produced by the V5ald6 pGPD1 control strain, and a corresponding increase in the production of 2,3-butanediol (FIG. 2). The V5 strain was used as a control. This strain does not build up acetoin and produces approximately 0.5 g/l of 2,3-butanediol.

FIG. 2 shows the acetoin levels obtained after several fermentation experiments with the V5ald6 pGPD1 and V5ald6 BDH1 pGPD1 strains, under the same conditions as above.

In Vitro Site-Directed Mutagenesis of BDH1

Starting from the protein sequence encoded by the BDH1 gene of the S288C strain [*Saccharomyces* genome database URL:yeastgenome[dot]org[slash]], mutations corresponding to the change of one amino acid were introduced at each PCR step. By means of oligonucleotides comprising the desired mutations and a plasmid containing the native BDH1 of S288C (pYES2-BDH1), the following mutated enzymes were constructed:

| | | |
|---|---|---|
| Wild-type enzyme: | BDH1 of S288C | 221 EIAERR 226 |
| Single mutant: | E221S | 221 SIAERR 226 |
| Double mutant: | E221S/I222R | 221 SRAERR 226 |
| Triple mutant: | E221S/I222R/A223S | 221 SRSERR 226 |

Site-Directed Mutagenesis

The mutations were introduced using a method based on the Quickchange II XL Site-Directed Mutagenesis Kit (Stratagene, USA). The E221S mutant was constructed from the coding region of BDH1 of the laboratory strain S288C cloned into the pYES2 plasmid (Invitrogen, Carlsbad, Calif.): pYES2-BDH1 (E. Gonzalez, 2000). This shuttle vector contains an inducible promoter (promoter and UAS sequence of GAL1), the 2μ origin of replication, the URA3 selectable marker and the bacterial elements (origin of replication and ampicillin-resistance gene).

The pYES2-BDH1 plasmid containing the E221S, E221S/I222R and E221S/I222R/A223S mutations was used as a template to obtain the single mutant, the double mutant and the triple mutant, respectively.

The mutagenesis was carried out by PCR using oligonucleotides containing the mutations (in bold) in the forward direction and in the reverse direction (E221S: MUT 221-1 (SEQ ID No. 3), MUT 221-2 (SEQ ID No. 4); E221S/I222R: MUT 222-1 (SEQ ID No. 5), MUT 222-2 (SEQ ID No. 6); E221S/I222R/A223S: MUT 223-1 (SEQ ID No. 7), MUT 223-2 (SEQ ID No. 8)).

```
SEQ ID No. 3 (MUT223221-1)
5' GGGCTAGTAAAATTGTAGTGTCTTCAATTGCAGAGAGAAGAATAGAA

ATGG 3',

SEQ ID No. 4 (MUT223221-2)
5' CCATTTCTATTCTTCTCTCTGCAATTGAAGACACTACAATTTTACTA

GCCCC 3'

SEQ ID No. 5 (MUT224222-1)
5' GGGGCTAGTAAAATTGTAGTGTCTTCAAGAGCAGAGAGAAGAATAGA

AATGG 3'

SEQ ID No. 6 (MUT224222-2)
5' CCATTTCTATTCTTCTCTCTGCTCTTGAAGACACTACAATTTTACTA

GCCCC 3'

SEQ ID No. 7 (MUT225223-1)
5' GGGGCTAGTAAAATTGTAGTGTCTTCAAGATCAGAGAGAAGAATAGA

AATGG 3'

SEQ ID No. 8 (MUT225223-2)
5' CCATTTCTATTCTTCTCTCTGATCTTGAAGACACTACAATTTTACTA

GCCCC 3'
```

*Escherichia coli* cells (ultracompetent XL-10 Gold®, Stratagène, La Jolla, Calif.) were transformed successively with the constructed plasmids. The transformants were cultured at 37° C. in 5 ml of LB medium supplemented with 50 μg/ml of ampicillin, and the plasmid DNA of these clones was extracted with the Genelute Plasmid Miniprep® kit (Sigma, USA) and analyzed by sequencing.

Transformation

The laboratory strain FY834 bdh1Δ (MATα his3Δ200 ura3-52 leu2Δ1 lys2Δ trp1Δ) was transformed with pYES2-BDH1, pYES2-MUT 221, pYES2-MUT 222, pYES2-MUT 223. The transformation method used is the lithium acetate method described by Schiestl and Gietz (1989). The selective medium used to select the strains transformed with the plasmids is YNB (0.67% yeast nitrogen base, 2% glucose) supplemented with histidine, leucine, lysine and tryptophan.

The absence of uracil makes it possible to maintain a selection pressure for the plasmids.

Culture Conditions 20 ml of YNB medium (20% galactose) were inoculated with 5 transformants, respectively. The culturing was carried out at 28° C. for 2 days.

Enzymatic Activity Assay

The butanediol dehydrogenase activity was determined using the crude protein extracts at 25° C., by measuring the change in absorbance at 340 nm. One activity unit corresponds to 1 μmol of cofactor used per min, based on an absorption coefficient of 6220 cm$^{-1}$ M$^{-1}$ at 340 nm for NADH and NADPH. The optical paths for the reduction reactions were 1 cm, 0.5 cm and 0.2 cm. The enzymatic activity assays were carried out in the presence of 50 mM of acetoin in 33 mM NaH$_2$PO$_4$, pH 7.0/NaOH. The kinetic parameters were obtained by means of assays of activity with coenzyme concentrations of ⅓×K$_m$ to 10×K$_m$ of BDH for NADH (0.055 mM).

The BDH activity was determined on crude extracts of the strain expressing the wild-type form (pYES2-BDH1) and of the strains expressing the mutated forms. The kinetic parameters of the various forms were also determined (table 2).

The three mutants exhibit an affinity for NADH that is very greatly reduced, by 90% on average relative to that of the native enzyme.

TABLE 2

| | SA (μmol/min · mg) | K$m_a$ (mM) |
|---|---|---|
| NADH | | |
| BDH | 4.9 ± 0.8 | 0.04 ± 0.00 |
| BDH221 | 0.5 ± 0.1 | ND |
| BDH222 | 0.7 ± 0.2 | ND |
| BDH223 | 0.3 ± 0.2 | ND |
| NADPH | | |
| BDH | Not detected | — |
| BDH221 | 1.0 ± 0.1 | 0.12 ± 0.02 |
| BDH222 | 4.6 ± 0.1 | 0.24 ± 0.14 |
| BDH223 | 5.6 ± 0.7 | 0.15 ± 0.01 |

ND: Not detected

A substantial reversion of the cofactor specificity from NADH to NADPH is observed for all the mutants (table 2). In fact, the mutants all exhibit an NADPH-dependent activity.

The apparent affinity constant ($Km_a$) for NADPH is of the same order for the three mutants.

The data as a whole show that the mutations made very greatly reduce the NADH-dependent activity of the enzyme and introduce an affinity for NADPH. The three mutants exhibit a similar affinity for NADPH. On the other hand, the double-mutant and triple-mutant forms are particularly advantageous because they have a better specific activity compared with the single mutant.

In order to evaluate the impact of the change in BDH cofactor in the enological model strain V5ald6, the BDH1 gene carrying the triple mutation, called $BDH1_{223}$, was overexpressed in this strain by in situ site-directed mutagenesis. Two oligonucleotides, including one of 55 base pairs (SEQ ID No. 9) containing the target mutations, were synthesized and used to amplify the loxpKanMXloxp-TDH3p-BDH1 region of a V5ald6 BDH1 strain. The amplified fragment, containing the KanMX marker and, under the control of the TDH3 promoter, the BDH1 gene up to the region containing the 3 mutations, was used to transform a V5ald6 strain.

This strategy made it possible, in a single step, to integrate the target mutations into the genomic sequence of Bdh1p, by homologous recombination, while at the same time overexpressing the mutated gene.

SEQ ID No. 1
5' CTTTCCTCCT TACGGGGTCC TAGCCTGTTT CTCTTGATAT

GCAGGTCGAC AACCCTTAAT

SEQ ID No. 9
5' GGCCATTTCTATTCTTCTCTGATCTTGAAGACACTACAATTTTAC

TGGCCCCC

Experimental conditions used for the PCR:

| | |
|---|---|
| Oligonucleotide (1) | 5 µl (20 pmol) |
| Oligonucleotide (2) | 5 µl (20 pmol) |
| 10X Taq buffer + 15 mM MgCl$_2$ | 5 µl |
| 2.5 mM dNTP | 4 µl |
| Total V5ald6 BDH1 DNA | 2 µl (50 ng/µl) |
| H$_2$O | 28.25 µl |
| Taq | 0.75 µl |

30 cycles (10 cycles: 20 sec 94° C., 20 sec 60° C., 3 min 72° C.; 20 cycles: 15 sec 94° C., 30 sec 60° C., 2 min + 20 s/cycle 72° C.).

The PCR product obtained was precipitated with ethanol in the presence of salts. 4 µg of the precipitated DNA were used to transform the *S. cerevisiae* V5ald6 yeast strains.

The integration was verified by enzymatic digestion of the PCR product for 2 hours at 37° C. with the Bbs I enzyme using the following reaction mixture: 13.5 µl of PCR product; 1.5 µl of 10×NEB2 buffer (Biolabs, USA); 0.25 µl (1.25 U) of Bbs I (Biolabs, USA).

The enzymatic activity was then determined on the crude protein extract of a strain having integrated the desired mutations. For each assay, 20 µl of crude extract were used in the presence of 0.2 mM of NADH/NADPH and 50 mM of acetoin.

In parallel, the modified region was sequenced, thereby making it possible to verify that the mutated BDH1 sequence is identical to the sequence of the native gene, with the exception of the mutations introduced, which result in 3 amino acids being changed in the protein (FIG. 3).

Physiological Impact of the Change in Cofactor Specificity of Bdh1

The V5ald6 BDH1 pGPD1 strain, overexpressing wild-type Bdh1, was compared with the clone having the NADPH-dependent Bdh1 (V5ald6 $BDH1_{223}$ pGPD1) in enological fermentation on a synthetic must at 200 g/l of glucose. These 2 strains were studied in fermentation in the absence of uracil (selection pressure).

Under these conditions, the fermentation-rate and biomass profiles are identical. No significant effect is observed on the fermentative by-products, except for an increase in the formation of α-ketoglutarate (from 480 mg/l to 620 mg/l), of OH-glutarate (from 1400 mg/l to 1620 mg/l) and of glycerol (from 30.2 g/l to 32.2 g/l) in the strain overexpressing the mutated Bdh compared with the native Bdh. The increase in glycerol formation can be explained by a greater availability of NADH, owing to the preferential use of NADPH by $Bdh1_{223}$. The buildup of alpha-ketoglutarate may be linked to the limitation of its reduction to glutamate, a reaction which is catalyzed by NADPH-dependent glutamate dehydrogenase Gdh1p. On the other hand, the production of OH-glutarate, another reduced product of alpha-ketoglutarate, could be the result of the greater availability of NADH. These observations clearly show an in vivo effect of the change in cofactor for BDH1, from NADH to NADPH.

The most striking effect obtained with the change in cofactor specificity is a very significant reduction in the production of acetoin in the V5ald6 $BDH1_{223}$ pGPD1 strain compared with the amount produced by V5ald6 BDH1 pGPD1. Under the conditions tested, this reduction is approximately 400 mg/l (FIG. 4).

The inventors furthermore showed that this effect was also obtained in another genetic background, the *S. cerevisiae* laboratory strain CEN.PK. Specifically, the overexpression of $BDH_{223}$ in CEN.PK ald6 pGPD1, which produces 1638 mg/l of acetoin on a synthetic must containing 50 g/l of glucose, results in a 68% reduction in acetoin production, whereas overexpression of the native enzyme reduces this production by only 18%. The amount of 2,3-butanediol increases stoichiometrically as the acetoin decreases (FIG. 5).

This clearly shows a physiological effect linked to the change in cofactor specificity of Bdh1 at high concentrations of glycerol. Not only is the amount of Bdh1 enzyme limiting in strains overproducing glycerol, but also the availability of NADH.

The invention thus provides wild-type and mutated yeast strains which overproduce 2,3-butanediol dehydrogenase, including strains which overproduce glycerol, with controlled production of acetate, which build up 2,3-butanediol in large amount and with a considerably reduced production of acetoin.

As the above examples show, the overexpression of BDH1 via in situ replacement of its promoter with that of TDH3 proves to be very effective, since an increase in activity by a factor of 30 was obtained. The analysis of these strains over the course of enological fermentation shows, moreover, that the level of expression of BDH1 and of enzymatic activity of BDH is indeed a limiting factor in the conversion of acetoin to 2,3-butanediol in strains which overproduce glycerol.

These results show that the conversion of acetoin to 2,3-butanediol is also limited by the availability of NADH. In fact, the overexpression of a mutated form of BDH that is NADPH-dependent creates an additional decrease in acetoin compared with a strain overexpressing the wild-type enzyme.

Thus, the strategy followed according to the invention, of overexpression of BDH1 and of change in cofactor specificity of BDH, from NADH to NADPH, enables an extremely efficient conversion of acetoin to 2,3-butanediol.

The strategy of $BDH1_{223}$ overexpression may be envisioned for reducing the acetoin in any modified or unmodified yeast strain that builds up this compound, such as strains which overproduce glycerol. Another example is a strain overexpressing a bacterial NADH oxidase. It has in fact been shown that overexpression of the NOXE gene encoding NADH oxidase of *Lactococcus lactis*, in the V5 strain, decreases the intracellular NADH content, thereby leading to a decrease in the ethanol yield owing to the limitation of the alcohol dehydrogenase activity. In this strain, the carbons not directed to the formation of ethanol build up at the acetaldehyde junction, in particular acetoin (Heux et al., 2006). The expression of a mutated form of BDH that uses NADPH as a cofactor, promoting the conversion of acetoin to 2,3-butanediol, could reduce the production of this compound.

The other mutants described above, which exhibit an increased affinity with respect to NADPH, in particular the double mutant which has the same characteristics as the triple mutant, may also prove to be advantageous for reducing acetoin under physiological conditions.

The expression of an NADPH-dependent Bdh1p in yeast makes it possible to modify the NADP/NADPH cofactor balance and, in this respect, may constitute an advantageous tool in the study of the intracellular oxidoreduction equilibrium.

BDH1 in Yeast: Interspecies and Intraspecies Sequence Homologies

The change in specificity of BDH was carried out in the S288C and V5 strains, although the cofactor binding site differs by one amino acid between these 2 strains. The V5 strain in fact has a valine at position 222, whereas S288C has an isoleucine at the same position. In each of these strains, the introduction of the E221S, E221S/I(V)222R and E221S/I222R/A223S mutations proved to be effective and made it possible to obtain a complete change in cofactor specificity from NADH to NADPH.

The conservation of this site was analyzed in other strains of *Saccharomyces cerevisiae* in which the genome has been sequenced (URL: sanger[dot]ac[dot]uk[slash]gbrowse [slash]gbrowse[slash]Saccharomyces[slash]).

The study shows that the 12 strains analyzed can be divided up into 2 groups, one (DBVPG1373, DBVPG1853, DBVPG6765, L__1374, L__1528 and SK1) characterized by the 221 EVA 223 sequence (V5-type sequence), the other (DBVPG6044, S288C, Y55, YGPM, YPS128 and YPS606) by the 221 EIA 223 sequence (S288C-type sequence). These observations indicate that the effects of the site-directed mutagenesis, described above, can extend to the other strains of *S. cerevisiae*.

Similarly, the sequence homologies of Bdh1p (S288C) with other yeast species (URL: cbi[dot]labri[dot]fr[slash] Genolevures[slash]path[slash]) were searched. 5 orthologous BDH1 genes were found in *Candida glabrata*, *Kluyveromyces lactis* and *Debaryomyces hansenii*. The protein sequence alignment shows a very strong conservation of the NADH-binding site, amino acids 221 and 223 being identical to those of *S. cerevisiae*. The position of amino acid 222 is more variable, as observed between *S. cerevisiae* strains. In the case of non-*Saccharomyces* yeasts, this amino acid is a proline, which is of the same family (hydrophobic aliphatic amino acids) as isoleucine or valine.

Owing to this sequence similarity, the amino acid changes by site-directed mutagenesis, described above, and the effects thereof, may be entirely applied to yeast species other than *S. cerevisiae*.

Other Example of Characterization of the Enzymatic Properties of the Mutated Forms of Bdh1p Transformation The laboratory strain WV36-405 (Mata, ade2, ura3-52, trp1, adh1 Δ, adh2 Δ, adh3 Δ, adh4:: TRP1) (Atrian et al., 1990) was also transformed with pYes2, pYes2-BDH1, pYes2-MUT 221, pYes2-MUT 222 and pYes2-MUT 223 by the described lithium acetate transformation method (Schiestl & Gietz, 1989). The selective medium used to select the transformed strains is YNB (0.67% yeast nitrogen base, 2% glucose) supplemented with adenine.

Culture Conditions and Preparation of Crude Extracts 20 ml of YNB medium (2% galactose) were inoculated with the transformants. The cells were taken in the growth phase, at OD (600 nm) 2.5. The cells ($10^9$) were suspended in 500 μl of buffer A (20 mM sodium phosphate (pH 7.0) containing 1% glycerol and 0.5 mM DTT) and ground using glass beads. After centrifugation at 12 000 rpm for 5 min, the supernatant was recovered and used for the enzymatic assays.

Enzymatic Activity Assay

The 2,3-butanediol dehydrogenase activity was determined using the crude extracts by measuring the change in absorbance at 340 nm as described below. The assays were carried out in the presence of 33 mM of sodium phosphate (pH 7.0), 0.5 mg/l of BSA (bovine serum albumin), of acetoin and of 1 mM NAD(P)H. The protein concentration in the extracts was determined with the Bradford method (Bio-Rad). The $K_m$ and $V_m$ for NAD(P)H (table 3) were determined in the presence of 50 mM and 450 mM of acetoin for Bdh1 and the Bdh1 mutants, respectively.

TABLE 3

| Enzyme | $K_m$ (μM) | $V_m$ (U/mg) | $V_m/K_m$ (ml mg$^{-1}$ min$^{-1}$) |
|---|---|---|---|
| NADH ||||
| Bdh1 | 45 ± 4 | 94 ± 1.7 | 2090 ± 194.0 |
| Bdh1$_{221}$ | 700 ± 20 | 9 ± 0.1 | 12 ± 0.3 |
| Bdh1$_{222}$ | n.s | n.s | n.d |
| Bdh1$_{223}$ | n.s | n.s | n.d |
| NADPH ||||
| Bdh1 | | n.d | |
| Bdh1$_{221}$ | 87 ± 6 | 15 ± 0.2 | 178 ± 12 |
| Bdh1$_{222}$ | 44 ± 4 | 59 ± 1.0 | 1347 ± 130 |
| Bdh1$_{223}$ | 44 ± 10 | 105 ± 1.5 | 2392 ± 157 | n.s: no saturation with up to 1 mM NADH
n.d: not determined

The specific activities with NADH and NADPH are given in table 4.

TABLE 4

| | Specific activity (U/mg) ||
|---|---|---|
| Enzyme | NADH (1 mM) | NADPH (1 mM) |
| Bdh1 | 92.0 ± 0.2 | 0.1 ± 0.0 |
| Bdh1$_{221}$ | 4.1 ± 1.4 | 13.7 ± 0.5 |
| Bdh1$_{221,222}$ | 4.8 ± 1.7 | 54.7 ± 1.9 |
| Bdh1$_{221,222,223}$ | 6.1 ± 0.1 | 93.2 ± 3.5 |

The mutants all exhibit an NADPH-dependent activity (tables 3 and 4). The affinity of the double-mutant and triple-mutant forms for NADPH (44 μM) is identical to the affinity of Bdh1 for NADH (45 μM). The comparison of the specific activities of each enzyme in the presence of 1 mM NAD(P)H (table 3) shows that the triple-mutant form has a substantially higher activity for NADPH than the double mutant.

Functioning of the Mutant Forms In Vivo

In order to evaluate the functioning, in vivo, of the NADPH-dependent mutant Bdh1 forms, the laboratory strain ENYpgi1 (MATa, ura3-52, leu2-3, trp1-289, his-Δ1, MAL2-8c, MAL3, SUC3, pgi1::KanMX) (Heux et al., 2008) was transformed with pYes2, pYes2-BDH1, pYes2-MUT 221, pYes2-MUT 222 and pYes2-MUT 223. The transformants were selected on uracil-free minimal medium containing 2% of fructose and 0.05% of glucose.

Drop tests were carried out using cells taken in the exponential growth phase at $OD_{600}$ 1. The cells were serially diluted 10-fold, and 10 µl of each dilution were deposited on YEP (1% yeast extract, 2% peptone) agar medium with 2% fructose plus 0.05% galactose; YEP agar medium with 0.5% galactose or YEP agar medium with 0.5% galactose plus 0.05%, 0.1% or 0.2% acetoin.

The ENYpgi1 strain is deleted of PGI1 which encodes phosphoglucose isomerase. This enzyme is located at the junction of glycolysis and the pentose phosphate pathway (PPP). In this mutant, glucose-6-phosphate is entirely redirected to the PPP, thereby generating an excess of NADPH which prevents the strain from developing. On the other hand, this mutant can develop if it is provided with an NADPH reoxidation system, for example provided by expression of the E. coli transhydrogenase udha.

In fact, FIG. 6 shows that ENYpgi cannot grow on galactose as the sole carbon source, whereas the expression of udha makes it possible to restore its growth. If acetoin is added to the culture medium (FIG. 6c), the growth of ENYpgi1 expressing the NADPH-dependent mutated forms of Bdh1 is also restored. It follows from these results that the NADPH-dependent BDH forms are capable of reoxidizing the NADPH produced in excess by this strain, to NADP, thereby demonstrating their functionality in vivo.

Overexpression of BDH1 in Order to Reduce Diacetyl Formation

Diacetyl (2,3-butanedione) is undesirable in fermented beverages. In wine, its detection threshold ranges between 0.2 and 2.8 mg/l, and it is considered to be undesirable above 5 mg/l. In beer, diacetyl poses a major problem owing to its very low detection threshold (0.1 ppm) and a long maturation stage is necessary in order to eliminate this compound.

Diacetyl comes from the oxidative decarboxylation of α-acetolactate, an intermediate in the biosynthesis of isoleucine, leucine and valine, and can be reduced to acetoin. It has been shown that Bdh1 has, in vitro, a diacetyl-reducing activity. In order to study the impact of Bdh1 on diacetyl in vivo, the final concentration of diacetyl produced by the V5ald6 pGPD1 and V5ald6 BDH1 pGPD1 strains in the experiment described in FIG. 2a was assayed.

The diacetyl concentration was determined by SPME (solid-phase microextraction) using deuterated diacetyl-d6 as internal standard, and GC-MS (Hayasaka & Bartowsky, 1999). The overexpression of BDH1 makes it possible to reduce the production of diacetyl by a factor of 2 (FIG. 7). Similar results were obtained with a strain overexpressing the triple-mutant form of Bdh1.

LITERATURE REFERENCES

Gonzalez, E., Fernandez, M. R., Larroy, C., Sola, L., Pericas, M. A., Pares, X. and Biosca, J. A., 2000. Characterisation of a (2R,3R)-2,3-Butanediol Dehydrogenase as the *Saccharomyces cerevisiae* YAL060W Gene Product. *J. Biol. Chem.* 275: 35876-35885.

Remize, F., Roustan, J. L., Sablayrolles, J. M., Barre, P. and Dequin, S., 1999. Glycerol Overproduction by Engineered *Saccharomyces cerevisiae* Wine Yeast Strains Leads to Substantial Changes in By-Product Formation and to a Stimulation of Fermentation Rate in Stationary Phase. *Appl. Environ. Microbiol.* 65: 143-149.

Güldener, U., Heck, S., Fiedler, T., Beinhauer, J. and Hegemann, J. H., 1996. A new efficient gene disruption cassette for repeated use in budding yeast. *Nucl. Ac. Res.* 24: 2519-2524 Schiestl, R. H. and R. D. Gietz, 1989. High efficiency transformation of intact cells using single stranded nucleic acid as carrier. *Curr. Genet.* 16: 339-446.

Bely, M., Sablayrolles J. M. and P. Barre, 1990. Automatic detection of assimilable nitrogen deficiencies during alcoholic fermentation in enological conditions. *J. Ferm. Bioeng.* 70: 246-252.

Michnick, S., Roustan, J. L., Remize, F., Barre, P., Dequin, S., 1997. Modulation of glycerol and ethanol yields during alcoholic fermentation in *Saccharomyces cerevisiae* strains overexpressed or disrupted for GPD1 encoding glycerol-3-phosphate dehydrogenase. *Yeast* 13: 783-793.

Heux, S., Cachon, R., Dequin, S., 2005. Cofactor engineering in *Saccharomyces cerevisiae*: expression of a H20-forming NADH oxidase and impact on metabolic flux redistribution. *Metab. Eng.*

Heux, S., Sablayrolles, J. M., Cachon, R. and Dequin, S., (2006) Engineering *S. cerevisiae* wine yeast with reduced ethanol production during fermentation under controlled microoxygenation conditions. *Appl. Environ. Microbiol.* 72: 5822-5828

Lundquist, F., (1974). Acetaldehyd: Bestimmung Mit Aldehyd-dehydrogenase. *Methods of Enzymatic Analysis.*, Academic Press, Inc., pp. 1509-1513.

Schiestl, R. H. & Gietz, R. D. (1989). High efficiency transformation of intact yeast cells using single stranded nucleic acids as a carrier. *Curr Genet.* 16, 339-346.

Heux, S., Cadiere, A. & Dequin, S. (2008). Glucose utilization of strains lacking PGI1 and expressing a transhydrogenase suggests differences in the pentose phosphate capacity among *Saccharomyces cerevisiae* strains. *FEMS Yeast Res.* 8, 217-24.

Hayasaka and Bartowsky (1999). Analysis of diacetyl in wine using solid-phase microextraction combined with gas chromatography-mass spectrometry. *J Agric Food Chem* 47, 612-617.

The invention claimed is:

1. An isolated *Saccharomyces cerevisiae* yeast strain in which the BDH1 gene encoding Bdh1p is overexpressed relative to the initial strain, wherein the overexpression results in an increase of the reduction of acetoin to 2,3-butanediol catalysed by Bdh1p at a rate that is at least twice that of the initial strain, said BDH1 gene is a mutated BDH1 gene comprising one or more mutations such that said gene encodes a Bdh1p protein in which one or more amino-acids are mutated in at least one of positions 221, 222 and 223 corresponding to a 221 SRS 223 fragment with reference to the *Saccharomyces cerevisiae* S288C strain, said mutation producing a Bdh1p protein having an increased affinity for NADPH as compared to the affinities of the Bdh1p protein without said mutation.

2. The yeast strain of claim 1, wherein the protein encoded by the mutated BDH1 gene comprises 3 mutations at position 221, 222 and 223, corresponding to a 221 SRS 223 fragment with reference to the *Saccharomyces cerevisiae* S288C strain.

3. An isolated *Saccharomyces cerevisiae* yeast strain in which the BDH1 gene encoding Bdh1p is overexpressed relative to an initial strain, wherein the overexpression results in an increase of the reduction of acetoin to 2,3-butanediol catalyzed by Bdh1p at a rate that is at least twice that of the initial strain, wherein the BDH1 gene comprises mutations at positions 221, 222 and 223.

4. The yeast strain as claimed in claim 1, characterized in that it overproduces glycerol.

5. The yeast strain as claimed in claim 4, characterized in that it comprises an overexpressed GPD1 gene or an overexpressed GPD2 gene.

6. The yeast strain as claimed in claim 1, characterized in that it is a genetically modified strain capable of reducing the amount of acetate produced in comparison with the strain as claimed in claim 5.

7. The yeast strain as claimed in claim 6, characterized in that the ALD6 gene has been deleted, and optionally copies thereof are also deleted.

8. The yeast strain as claimed in claim 3, characterized in that it overproduces glycerol.

9. The yeast strain as claimed in claim 8, characterized in that it comprises an overexpressed GPD1 gene or an overexpressed GPD2 gene.

* * * * *

SEQUENCE LISTING

```
<160> NUMBER OF SEQ ID NOS: 11

<210> SEQ ID NO 1
<211> LENGTH: 60
<212> TYPE: DNA
<213> ORGANISM: Artificial sequence
<220> FEATURE:
<223> OTHER INFORMATION: oligonucleotide

<400> SEQUENCE: 1
ctttcctcct tacggggtcc tagcctgttt ctcttgatat gcaggtcgac aaccettaat    60
```

<210> SEQ ID NO 2
<211> LENGTH: 61
<212> TYPE: DNA
<213> ORGANISM: Artificial sequence
<220> FEATURE:
<223> OTHER INFORMATION: oligonucleotide

<400> SEQUENCE: 2
agtgaatatc accettcttg aaatatgcca aagctctcat tcgaaactaa gttcttggtg    60
t    61

<210> SEQ ID NO 3
<211> LENGTH: 51
<212> TYPE: DNA
<213> ORGANISM: Artificial sequence
<220> FEATURE:
<223> OTHER INFORMATION: oligonucleotide

<400> SEQUENCE: 3
gggctagtaa aattgtagtg tcttcaattg cagagagaag aatagaaatg g    51

<210> SEQ ID NO 4
<211> LENGTH: 52
<212> TYPE: DNA
<213> ORGANISM: Artificial sequence
<220> FEATURE:
<223> OTHER INFORMATION: oligonucleotide

<400> SEQUENCE: 4
ccatttctat tcttctctct gcaattgaag acactacaat tttactagcc cc    52

<210> SEQ ID NO 5
<211> LENGTH: 52
<212> TYPE: DNA
<213> ORGANISM: Artificial sequence
<220> FEATURE:
<223> OTHER INFORMATION: oligonucleotide

<400> SEQUENCE: 5
ggggctagta aaattgtagt gtcttcaaga gcagagagaa gaatagaaat gg    52

<210> SEQ ID NO 6
<211> LENGTH: 52
<212> TYPE: DNA
<213> ORGANISM: Artificial sequence
<220> FEATURE:
<223> OTHER INFORMATION: oligonucleotide

<400> SEQUENCE: 6
ccatttctat tcttctctct gctcttgaag acactacaat tttactagcc cc    52

<210> SEQ ID NO 7
<211> LENGTH: 52
<212> TYPE: DNA
<213> ORGANISM: Artificial sequence
<220> FEATURE:
<223> OTHER INFORMATION: oligonucleotide

<400> SEQUENCE: 7
ggggctagta aaattgtagt gtcttcaaga tcagagagaa gaatagaaat gg    52

<210> SEQ ID NO 8
<211> LENGTH: 52
<212> TYPE: DNA

<213> ORGANISM: Artificial sequence
<220> FEATURE:
<223> OTHER INFORMATION: oligonucleotide

<400> SEQUENCE: 8
ccatttctat tcttctctct gatcttgaag acactacaat tttactagcc cc        52

<210> SEQ ID NO 9
<211> LENGTH: 55
<212> TYPE: DNA
<213> ORGANISM: Artificial sequence
<220> FEATURE:
<223> OTHER INFORMATION: oligonucleotide

<400> SEQUENCE: 9
ggccatttct attcttctct ctgatcttga agacactaca attttactgg ccccc        55

<210> SEQ ID NO 10
<211> LENGTH: 382
<212> TYPE: PRT
<213> ORGANISM: Saccharomyces cerevisiae strain S288C

<400> SEQUENCE: 10

Met Arg Ala Leu Ala Tyr Phe Lys Lys Gly Asp Ile His Phe Thr Asn
1               5                   10                  15

Asp Ile Pro Arg Pro Glu Ile Gln Thr Asp Asp Glu Val Ile Ile Asp
            20                  25                  30

Val Ser Trp Cys Gly Ile Cys Gly Ser Asp Leu His Glu Tyr Leu Asp
        35                  40                  45

Gly Pro Ile Phe Met Pro Lys Asp Gly Glu Cys His Lys Leu Ser Asn
    50                  55                  60

Ala Ala Leu Pro Leu Ala Met Gly His Glu Met Ser Gly Ile Val Ser
65                  70                  75                  80

Lys Val Gly Pro Lys Val Thr Lys Val Lys Val Gly Asp His Val Val
                85                  90                  95

Val Asp Ala Ala Ser Ser Cys Ala Asp Leu His Cys Trp Pro His Ser
            100                 105                 110

Lys Phe Tyr Asn Ser Lys Pro Cys Asp Ala Cys Gln Arg Gly Ser Glu
        115                 120                 125

Asn Leu Cys Thr His Ala Gly Phe Val Gly Leu Gly Val Ile Ser Gly
    130                 135                 140

Gly Phe Ala Glu Gln Val Val Val Ser Gln His His Ile Ile Pro Val
145                 150                 155                 160

Pro Lys Glu Ile Pro Leu Asp Val Ala Ala Leu Ile Glu Pro Leu Ser
                165                 170                 175

Val Thr Trp His Ala Val Lys Ile Ser Gly Phe Lys Lys Gly Ser Ser
            180                 185                 190

Ala Leu Val Leu Gly Ala Gly Pro Ile Gly Leu Cys Thr Ile Leu Val
        195                 200                 205

Leu Lys Gly Met Gly Ala Ser Lys Ile Val Val Ser Glu Val Ala Glu
    210                 215                 220

Arg Arg Ile Glu Met Ala Lys Lys Leu Gly Val Glu Val Phe Asn Pro
225                 230                 235                 240

Ser Lys His Gly His Lys Ser Ile Glu Ile Leu Arg Gly Leu Thr Lys
                245                 250                 255

Ser His Asp Gly Phe Asp Tyr Ser Tyr Asp Cys Ser Gly Ile Gln Val
            260                 265                 270

```
Thr Phe Glu Thr Ser Leu Lys Ala Leu Thr Phe Arg Gly Thr Ala Thr
            275                 280                 285

Asn Ile Ala Val Trp Gly Pro Lys Pro Val Pro Phe Gln Pro Met Asp
290                 295                 300

Val Thr Leu Gln Glu Lys Val Met Thr Gly Ser Ile Gly Tyr Val Val
305                 310                 315                 320

Glu Asp Phe Glu Val Val Arg Ala Ile His Asn Gly Asp Ile Thr
            325                 330                 335

Met Glu Asp Cys Lys Gln Leu Ile Thr Gly Lys Gln Arg Ile Glu Asp
                340                 345                 350

Gly Trp Glu Lys Gly Phe Gln Glu Leu Met Asp His Lys Glu Ser Asn
            355                 360                 365

Val Lys Ile Leu Leu Thr Pro Asn Asn His Gly Glu Met Lys
        370                 375                 380
```

<210> SEQ ID NO 11
<211> LENGTH: 383
<212> TYPE: PRT
<213> ORGANISM: Artificial Sequence
<220> FEATURE:
<223> OTHER INFORMATION: Description of Artificial Sequence: BDH1223

<400> SEQUENCE: 11

```
Met Arg Ala Leu Ala Tyr Phe Lys Lys Gly Asp Ile His Phe Thr Asn
1               5                   10                  15

Asp Ile Pro Arg Pro Glu Ile Gln Thr Asp Glu Val Ile Ile Asp
            20                  25                  30

Val Ser Trp Cys Gly Ile Cys Gly Ser Asp Leu His Glu Tyr Leu Asp
        35                  40                  45

Gly Pro Ile Phe Met Pro Lys Asp Gly Glu Cys His Lys Leu Ser Asn
    50                  55                  60

Ala Ala Leu Pro Leu Ala Met Gly His Glu Met Ser Gly Ile Val Ser
65                  70                  75                  80

Lys Val Gly Pro Lys Val Thr Lys Val Lys Val Gly Asp His Val Val
                85                  90                  95

Val Asp Ala Ala Ser Ser Cys Ala Asp Leu His Cys Trp Pro His Ser
            100                 105                 110

Lys Phe Tyr Asn Ser Lys Pro Cys Asp Ala Cys Gln Arg Gly Ser Glu
        115                 120                 125

Asn Leu Cys Thr His Ala Gly Phe Val Gly Leu Gly Val Ile Ser Gly
    130                 135                 140

Gly Phe Ala Glu Gln Val Val Val Ser Gln His Ile Ile Pro Val
145                 150                 155                 160

Pro Lys Glu Ile Pro Leu Asp Val Ala Ala Leu Ile Glu Pro Leu Ser
                165                 170                 175

Val Thr Trp His Ala Val Lys Ile Ser Gly Phe Lys Lys Gly Ser Ser
            180                 185                 190

Ala Leu Val Leu Gly Ala Gly Pro Ile Gly Leu Cys Thr Ile Leu Val
        195                 200                 205

Leu Lys Gly Met Gly Ala Ser Lys Ile Val Val Ser Ser Arg Ser Glu
    210                 215                 220

Arg Arg Ile Glu Met Ala Lys Lys Leu Gly Val Glu Val Phe Asn Pro
225                 230                 235                 240

Ser Lys His Gly His Lys Ser Ile Glu Thr Leu Arg Gly Leu Thr Lys
                245                 250                 255
```

```
Ser His Asp Gly Phe Asp Tyr Ser Tyr Asp Cys Ser Gly Ile Gln Val
        260             265             270

Thr Phe Glu Thr Ser Leu Lys Ala Leu Thr Phe Arg Gly Thr Ala Thr
        275             280             285

Asn Ile Ala Val Trp Gly Pro Lys Pro Val Pro Phe Gln Pro Leu Met
        290             295             300

Asp Val Thr Leu Gln Glu Lys Val Met Thr Gly Ser Ile Gly Tyr Val
305             310             315                         320

Val Glu Asp Phe Glu Val Val Arg Ala Ile His Asn Gly Asp Ile
            325             330             335

Thr Met Glu Asp Cys Lys Gln Leu Ile Thr Gly Lys Gln Arg Ile Glu
            340             345             350

Asp Gly Trp Glu Lys Gly Phe Gln Glu Leu Met Asp His Lys Glu Ser
        355             360             365

Asn Val Lys Ile Leu Leu Thr Pro Asn Asn His Gly Glu Met Lys
        370             375             380
```